United States Patent [19]

Meyer

[11] 4,158,019
[45] Jun. 12, 1979

[54] METHYLGLYOXAL DIMETHYL ACETAL PRODUCTION

[75] Inventor: Karl Meyer, Liestal, Switzerland

[73] Assignee: Hoffmann-La Roche Inc., Nutley, N.J.

[21] Appl. No.: 860,534

[22] Filed: Dec. 14, 1977

Related U.S. Application Data

[63] Continuation of Ser. No. 707,157, Jul. 21, 1976, abandoned.

[51] Int. Cl.² ............................................. C07C 45/00
[52] U.S. Cl. .................................................... 260/594
[58] Field of Search ........................................ 260/594

[56] References Cited

U.S. PATENT DOCUMENTS

| 3,478,060 | 11/1969 | Maschke et al. | 260/594 |
| 3,965,191 | 6/1976 | Gupta | 260/594 |

OTHER PUBLICATIONS

Manning et al., J.A.C.S., vol. 81, pp. 4885–4890 (1959).
Manning et al., J. Org. Chem., vol. 28, pp. 1673–1675 (1963).
Freeman, Chem. Rev., vol. 73(4), pp. 283–292 (1973).

*Primary Examiner*—James H. Reamer
*Attorney, Agent, or Firm*—Jon S. Saxe; Bernard S. Leon; William H. Epstein

[57] ABSTRACT

A two-step procedure for the preparation of methylglyoxal dimethyl acetal is disclosed.

4 Claims, No Drawings

METHYLGLYOXAL DIMETHYL ACETAL PRODUCTION

This is a continuation of application Ser. No. 707,157, filed July 21, 1976 now abandoned.

BRIEF DESCRIPTION OF THE INVENTION

The present invention relates to a process for the manufacture of an acetal, namely methylglyoxal dimethyl acetal.

Previously, methylglyoxal dimethyl acetal has been manufactured by reacting a mixture of acetone and methanol with a nitrosating agent such as nitrous acid, dinitrogen trioxide or methyl nitrite in the presence of an acid catalyst, e.g., a strong inorganic acid or a Lewis acid.

It has now been found in accordance with the present invention that methylglyoxal dimethyl acetal can be manufactured in higher yields than realized heretofore when acetone is reacted with a nitrosating agent and the resulting isonitrosoacetone is isolated and then acetalized in the presence of a nitrosating agent and methyl alcohol.

Apart from the higher yields, an additional advantage of the present process is that because small amounts of high-boiling components are produced in the reaction, subsequent work-up is greatly simplified.

Accordingly, the process of this invention is comprised of two distinct steps with the isolation of the isonitrosoacetone in the first step being a fundamental aspect of this invention.

In the acetone nitrosation step, an alkali metal nitrite, preferably sodium nitrite, is used as the nitrosating agent in combination with an acid, e.g. a strong inorganic acid, such as hydrochloric acid, hydrobromic acid, sulfuric acid and phosphoric acid, preferably hydrochloric acid.

In the second step, the isonitrosoacetone obtained in the first step is acetalized. This acetalization is carried out by treating the isolated isonitrosoacetone with a lower alkanol, preferably methyl alcohol, methyl nitrite and a strong inorganic acid or a Lewis acid, preferably hydrochloric acid.

The present process can be illustrated by the following reaction scheme:

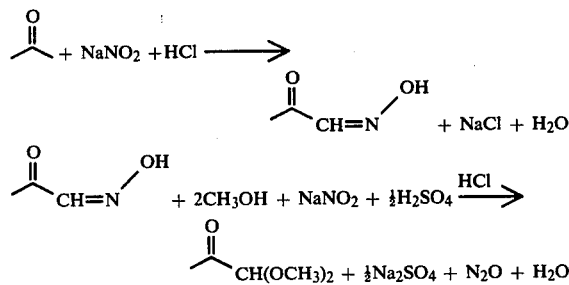

Although temperatures and pressures are not critical, it has been found that the process of this invention may be carried out at atmospheric pressure and temperatures ranging from about 0° C. to about 40° C., preferably 20° C. to about 40° C. for the first step. The temperature for the second step of this process may vary from −40° C. to about 0° C., preferably −20° C. to about −5° C.

A particularly preferred temperature for the second step is between about −10° C. and about −5° C.

The amount of acetone per mole of alkali metal nitrite may be from 6 to 20 moles. The amount of acid employed per mole of alkali metal nitrite may vary from 1.0 to 4 moles. In the acetalizing step there are generally employed 20 moles of methyl alcohol, 1.3 moles of alkali metal nitrite and 1.0 moles of strong acid per mole of isonitrosoacetone.

The methylglyoxal dimethyl acetal prepared in accordance with this invention may be used as an intermediate in the production of γ-acetoxy tiglic aldehyde, which is useful in the production of vitamin A.

The term "alkali metal" as used herein, includes sodium, potassium and lithium, sodium nitrite being preferred. The term "lower alkanol" denotes straight or branched chain alkanols containing 1–6 carbon atoms such as methanol, ethanol and the like.

The following non-limiting Examples illustrate the present invention. All temperatures are in degrees Centigrade.

EXAMPLE 1

696 g of acetone are introduced into a 2 liter 4-necked flask, fitted with a stirrer, a thermometer and a dropping funnel, and 115.6 g of concentrated hydrochloric acid are added dropwise at −30° C. over a period of 5 to 10 minutes. The resulting solution is then warmed to 20° C. 69 g of sodium nitrite dissolved in 80 ml of water are added dropwise from the dropping funnel over a period of 15 to 17 minutes at an internal temperature of about 20° C. to 30° C. During this addition, the mixture is cooled slightly with the temperature being carefully maintained above 20° C. At the conclusion of a 5 minute reaction period, the mixture is cooled to about 15° C. and neutralized with 26 ml of concentrated sodium hydroxide solution.

The excess acetone is then distilled from the mixture over a 75 minute period in a rotary evaporator at 20° C. and under a pressure of 15 mmHg. On evaporating the mixture the pH value falls. Care must be taken to insure that the pH is maintained at about 4.5. About 754 g of acetone distillate with an acetone content of 85% are recovered on evaporation, the remainder being water.

250 ml of methylene chloride are added to the remaining crystal sludge and the mixture is shaken. The organic phase is then separated off and the aqueous phase is extracted once with 250 ml of methylene chloride and eight times with 150 ml of methylene chloride. The combined organic phases are evaporated to dryness in a rotary evaporator at 30° C. and under a pressure of 400 mmHg. 83.1 g of crude isonitrosoacetone with a content of 94.2% and a water content of less than 0.5% are thus obtained. The yield, calculated relative to acetone, is 88%.

EXAMPLE 2

440 ml of absolute methanol are introduced into a 750 ml sulfonating flask fitted with a stirrer, a thermometer, a gas inlet tube, a bubble counter and 100 ml dropping funnel with a pressure balance and cooled to −5° C. 30.6 liters of gaseous hydrogen chloride are passed in over a period of 30 minutes. 4.2 g of sulfuric acid, 60 g of ice and 26 g of methanol are introduced into a 250 ml 4-necked flask. 53.8 g of sodium nitrite dissolved in 55 ml of water are passed into the resulting solution, below the surface, at about 5° C., maintained by cooling with an ice bath, over a period of 3 hours and 15 minutes. The methyl nitrite formed is passed over a calcium chloride drying tower, liquified in a spiral condenser, maintained at −25° C., and passed into the methanolic hydrochloric acid prepared above resulting in a pale yellow solution.

The temperature is allowed to rise up to −15° C. and 52.2 g of the isonitrosoacetone of Example 1 in 55 ml of absolute methanol are added dropwise to the yellow solution over a period of 45 minutes with vigorous stirring. Upon completion of the addition, the internal temperature is about −7° C. to about −10° C. The mixture is then warmed to room temperature with the concurrent escape of most of the dinitrogen oxide which is formed. The solution is diluted with 280 ml of water and added dropwise to 170 ml of a saturated sodium carbonate solution at room temperature over a period of 4 hours and 15 minutes. Sodium bicarbonate initially precipitates at the start of this neutralization, but the solution subsequently clears. The pH is adjusted to 6.5.

The aqueous solution is extracted once with 200 ml of methylene chloride and nine times with 80 ml of methylene chloride and five time with 50 ml of methylene chloride. The organic phase is washed once with 200 ml of water and once with 100 ml of water. About 1.6 kg of methylene chloride solution is recovered. The solution is concentrated to about 140 g in a rotary evaporator at 20° C. and under a pressure of 260 mmHg. The residual solvent is distilled off at 20° C. and 11 mmHg until less than 1.5% of methylene chloride can be detected by gas chromatography. About 68 g of crude methylglyoxal dimethyl acetal are obtained. After separation from the high-boiling by-products, by means of a thin layer evaporator under a pressure of 11 mmHg and at a mantle temperature of 50° C., 64.9 g of product containing 89% of methylglyoxal dimethyl acetal are obtained.

As a variation of the foregoing procedure, the isonitrosoacetone can be added to the methanolic hydrochloric acid solution and methyl nitrite is then rapidly passed into the mixture. In this procedure temperatures between about −20° C. and +40° C., preferably between about +10° C. and about +20° C., are employed.

I claim:

1. A process for the manufacture of methylglyoxal dimethyl acetal comprising reacting at a temperature of from about 0° C. to 40° C. acetone with a nitrosating agent composed of an alkali metal nitrite and an acid, isolating the resulting isonitrosoacetone and acetalizing, with methyl alcohol, at a temperature of from −40° C. to about +40° C., said isolated isonitrosoacetone in the presence of a nitrosating agent composed of alkali metal nitrite and an acid.

2. A process according to claim 1 wherein the alkali metal nitrite is sodium nitrite and the acid is hydrochloric acid.

3. A process according to claim 1 wherein the acetalization of the isonitrosoacetone is carried out by treatment of said isonitrosoacetone with methyl alcohol, methyl nitrite and an acid.

4. A process according to claim 3 wherein the acid is hydrochloric acid.

* * * * *

UNITED STATES PATENT AND TRADEMARK OFFICE
CERTIFICATE OF CORRECTION

PATENT NO. : 4,158,019
DATED : Jun. 12, 1979
INVENTOR(S) : Karl Meyer

It is certified that error appears in the above-identified patent and that said Letters Patent are hereby corrected as shown below:

Cover Sheet, after

"[22] Filed: Dec. 14, 1977" insert

[30]  Foreign Application Priority Data

August 13, 1975      Switzerland      10532/75

Signed and Sealed this

Twelfth Day of February 1980

[SEAL]

Attest:

SIDNEY A. DIAMOND

Attesting Officer     Commissioner of Patents and Trademarks